United States Patent
Wang et al.

(10) Patent No.: US 6,638,311 B2
(45) Date of Patent: Oct. 28, 2003

(54) PROSTHESIS BEARING COMPONENT

(75) Inventors: Aiguo Wang, Wayne, NJ (US); Eric Jones, Limerick (IE); Casper F. Stark, Pompton Lakes, NJ (US); John H. Dumbleton, Ridgewood, NJ (US); Ruey Lin, Concord, CA (US)

(73) Assignee: Benoist Girard SAS (FR)

( * ) Notice: Subject to any disclaimer, the term of this patent is extended or adjusted under 35 U.S.C. 154(b) by 10 days.

(21) Appl. No.: 10/008,287

(22) Filed: Nov. 5, 2001

(65) Prior Publication Data

US 2002/0111691 A1 Aug. 15, 2002

(30) Foreign Application Priority Data

Nov. 7, 2000 (GB) .............................. 0027210

(51) Int. Cl.[7] .................................. A61F 2/32
(52) U.S. Cl. .................. 623/22.32; 623/22.11
(58) Field of Search ............ 623/22.32, 22.11, 623/22.15, 22.21, 22.38

(56) References Cited

U.S. PATENT DOCUMENTS

| | | | |
|---|---|---|---|
| 2,910,978 A | 11/1959 | Urist | |
| 3,840,904 A | 10/1974 | Tronzo | |
| 4,743,262 A | 5/1988 | Tronzo | |
| 4,790,851 A | * 12/1988 | Suire et al. ............... | 128/898 |
| 5,181,930 A | 1/1993 | Dumbleton et al. | |
| 5,358,532 A | * 10/1994 | Evans et al. ............. | 623/22.23 |
| 5,443,513 A | 8/1995 | Moumene et al. | |
| 5,609,646 A | 3/1997 | Field et al. | |
| 5,782,930 A | 7/1998 | Lin et al. | |
| 5,879,387 A | 3/1999 | Jones et al. | |
| 5,879,406 A | * 3/1999 | Lilley ...................... | 623/22.15 |
| 5,904,720 A | 5/1999 | Farrar et al. | |
| 6,126,695 A | 10/2000 | Semlitsch | |
| 6,221,108 B1 | 4/2001 | Smith | |
| 2001/0027345 A1 | * 10/2001 | Merrill et al. ........... | 623/18.11 |

FOREIGN PATENT DOCUMENTS

| | | |
|---|---|---|
| DE | 44 37 479 A1 | 5/1996 |
| EP | 0 297 789 A1 | 1/1989 |
| FR | 2 635 968 | 3/1990 |
| WO | WO 99/03429 | 1/1999 |

* cited by examiner

Primary Examiner—Cary E. O'Connor
Assistant Examiner—Candice C. Melson
(74) Attorney, Agent, or Firm—Lerner, David, Littenberg, Krumholz & Mentlik, LLP

(57) ABSTRACT

According to the present invention a prosthetic bearing component is formed from a composite synthetic plastics material comprising an injection molded thermoplastic polymeric matrix reinforced by a pitch based carbon fiber and having a bearing surface which has been machined with a surface roughness with a value less than $R_a$ 2 μm. Such components have shown superior wear qualities. Preferably the bearing surface shape is machined with tolerances of 0.1 to 0.15 mm. The composite material must be capable of withstanding a radiation value of at least 2.8 Mega Rads (MRad). In components in which the bearing surface is substantially or part spherical a sphericity of 0.3 μm within a solid angle of 45° is required.

18 Claims, 2 Drawing Sheets

PROSTHESIS BEARING COMPONENT

BACKGROUND OF THE INVENTION

This invention relates to a prosthesis bearing component which can be utilized, for example, in a prosthetic hip socket.

Ultra-high molecular weight polyethylene (UHMWPE) has been used as a bearing surface for acetabular components and coupled with a metal or ceramic femoral head this material has shown excellent resistance to penetration wear. However, advances it total hip arthroplasty have shown that, although such sockets very rarely wear through, debris can be generated form it which can cause adverse tissue reactions.

In two papers published by Elsevier Science Ltd. in 1999 entitled "Suitability and limitations of carbon fiber reinforced PEEK composites as bearing surfaces for total joint replacements (A. Wang, R. Lin, C. Stark and J. H. Dumbleton) Tribiology International, Vol. 31, No. 11, pp 661–667, and "Carbon fiber reinforced polyether ether ketone composite as a bearing surface for a total hip replacement" (A. Wang, R. Lin, V. K. Polineni, A. Essner, C. Stark and J. H. Dumbleton) Wear (1999), Volume No. 225/229, pp. 724–727, the possibilities and advantages of using carbon fiber reinforced polyether ether ketone (PEEK) composite as a bearing surface for total replacements id discussed and analysed. These papers describe the manufacture of acetabular cups made from carbon fiber reinforced PEEK composite and conclude that such cups offer advantages over UHMWPE composite cups.

A carbon fiber reinforced composite acetabular cup is shown in U.S. Pat. No. 5,609,646 and a composite hip implant is shown in U.S. Pat. Nos. 5,181,930 and 5,443,513.

Further research now shows that even further advantages can be obtained with carbon fiber composite cups if certain steps are taken during manufacture.

SUMMARY OF THE INVENTION

According to the present invention a prosthetic bearing component is formed from a composite synthetic plastics material comprising an injection molded thermoplastic polymeric matrix reinforced by a pitch based carbon fiber and having a bearing surface which has been machined with an average surface roughness with a value less than an $R_a$ of 2 µm. Such components have shown superior wear qualities.

Preferably the bearing surface shape is machined with tolerances of 0.1 to 0.15 mm. The composite material must be capable of withstanding a radiation value of at least 2.8 Mega Rads (MRad) without degradation. Such radiation may be for sterilization purposes. In components in which the bearing surface is substantially or part spherical a sphericity of 0.3 µm within a solid angle of 45° is required.

The thermoplastic polymeric matrix can be a polyester, for example PVT (polyethylene tetraphthalate), a polyonylketone, for example PEEK (polyether ether ketone), or a polysulphone, for example polyethersulphone. It is also possible that other materials can be employed.

The bearing component can be in the form of a cementless bearing element having an outer surface which includes a number of raised engagement features.

These features can be provided in directions extending away from and/or towards the outer periphery of the outer surface and can be formed by projecting strakes of substantially triangular cross-section. Moreover, the outer surface can also carry one or more projecting fins.

BRIEF DESCRIPTION OF THE DRAWINGS

The invention has been found to be particular, although not exclusively, adaptable for use as a prosthetic hip cup and one embodiment of the invention as applied to a prosthetic hip cup will now be described by way of example and with reference to the accompanying drawings in which.

DETAILED DESCRIPTION

Figure 1:
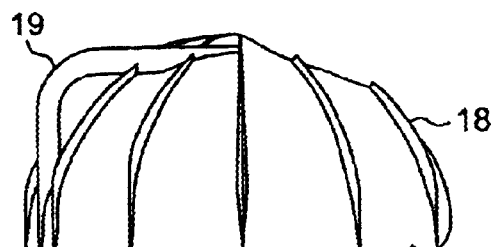
FIG. 1 is a side elevation of a prosthetic bearing element according to the invention.
Figure 2:
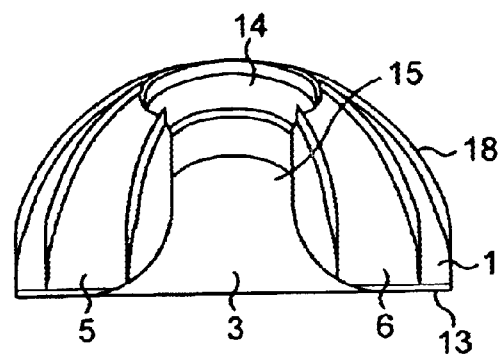
FIG. 2 is a front elevation of the element shown in FIG. 1.
Figure 3:
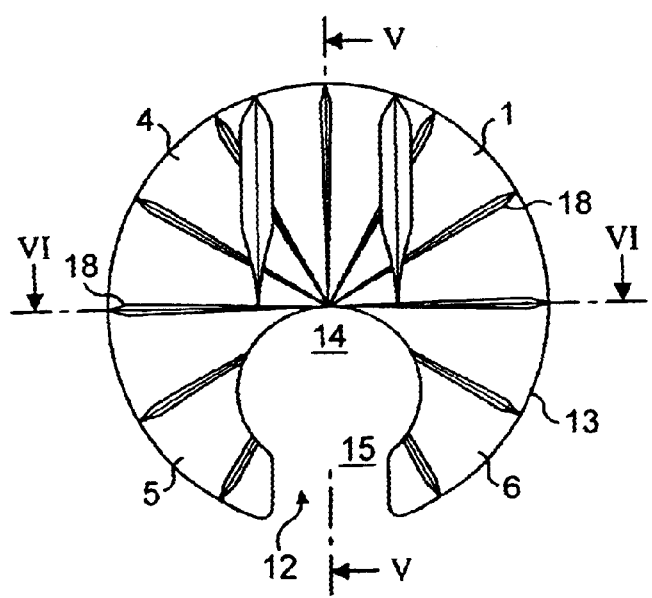
FIG. 3 is a plan view from above of the element shown in FIGS. 1 and 2.
Figure 4:
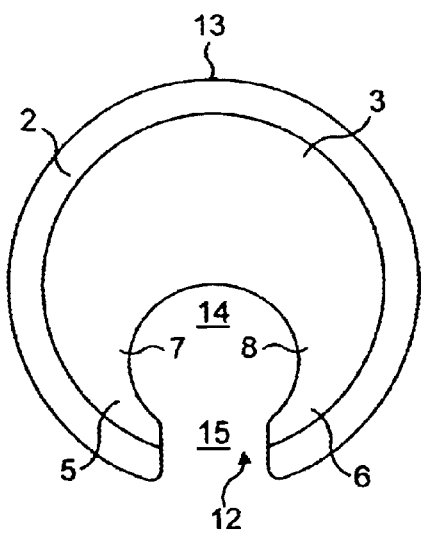
FIG. 4 is a plan view from below of the element shown in FIGS. 1–3.
Figure 5:
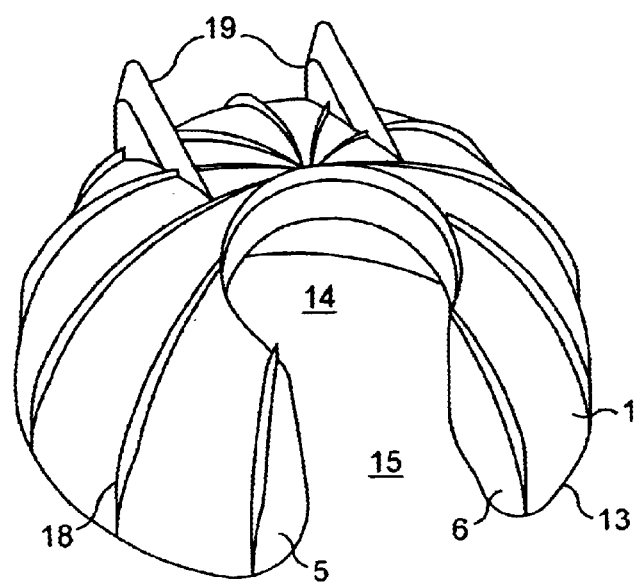
FIG. 5 is an isometric view from above of the element shown in FIGS. 1–4.
Figure 6:
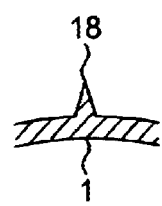
FIG. 6 is a part cross-sectional view showing an engagement feature.

As shown in FIGS. 1–6 a cementless prosthetic bearing element according to the invention comprises an acetabular cup 1 which is injection molded from a composite synthetic plastics material to provide a thermoplastic polymeric matrix reinforced by a pitch based carbon fiber. The cup has an outer rim 2 and a bearing surface 3 which is machined with a surface roughness with a value less than $R_a$ of 2 µm. This bearing surface 3 is machined with tolerances of 0.1 to 0.15 mm and the composite material is chosen so that it is capable of withstanding a radiation value of at least 2.8 Mega Rads (MRad).

As will be seen the bearing surface 3 is part-spherical and is machined to have a sphericity of 0.3 µm within a solid angle of 45°.

The thermoplastic polymeric matrix can be made from any suitable material, for example polyether ether ketone (PEEK) or polyethylene tetraphthalate.

In a typical example pitch based carbon fibers were mixed with a PEEK resin (ICI Grade 150 G) and then palletized. The carbon fibers were chopped fibers with an average diameter of 8 µm and an average length of 20 µm. The pellets were molded into an acetabular cup and the fiber loading in the specimens ranged from 10 Wt % to 50 Wt %.

The general overall shaped construction of the prosthesis is similar to that described in U.S. Pat. No. 5,609,646, the teachings of which are incorporated herein by reference, but does not have an outer backing and separate bearing liner. The main portion of the element 4 is substantially part spherical and there are two independent arms 5 and 6 which extend from the part 4. The bearing surface is only hemispherical over its main portion and is relieved (i.e. straight or non-spherical) over inner surfaces 7 and 8 of its arms 5 and 6.

If desired the element could be substantially hemispherical and merely carry a thin splitting line or slit to provide the two separate arms 5 and 6.

The arms 5 and 6 are spaced apart to provide a gap or opening 12 between them. They are spaced apart about an arc on the part-spherical main portion breaking out of the rim 13 of the main portion together. Both of the arms are substantially part-spherical.

The element therefore comprises a substantially part-spherical wall having a rim 13 which is interrupted by a shaped opening to provide the two spaced arms 5 and 6.

The main part 14 of the opening 12 is substantially semi-circular and has a mouth 15 which provides the interruption in the rim 13 and which is of smaller width than the remainder 14 of the opening. The element is therefore substantially horseshoe-shaped.

Because of its construction and the materials used it is sufficiently flexible to accept deformation of the acetabulum of the patient but is stiff enough to carry the ball of the prosthesis with which it is to cooperate.

It has been found that this particular shape of opening is convenient and successful when the loading is transferred onto the pelvis as required, in particular the shape of opening ensures efficiently that no load is transferred into the bone at an undesired location.

The outer surface of element 1 includes a number of raised engagement features which are provided in directions extending away from and/or towards the outer periphery 13 of the outer surface. Thus, the raised engagement features are in the form of projecting strakes 18 which extend radially from the outer periphery 13 and are of triangular cross-section and is most clearly shown in FIG. 6. Between the projecting strakes the surface is substantially part-spherical. In the preferred embodiment the strakes are located at 30° internals.

The outer surface also carries a pair of projecting fins 19 which extend in spaced apart parallel chordal directions.

The outer surface of the element may be plasma sprayed with hydroxyapatite (HA) coating which is osteoconductive and stimulates bone growth.

In order to insert this type of acetabular cup into an acetabulum the bone is first prepared to the appropriate shape and a series of triangular grooves are carved into it by the surgeon which will line up with the strakes on the cup. Similarly two cordal grooves are cut to accept the fins 19.

The cup is now placed in position and lightly tapped, the strakes and fins holding it accurately as required. The joint is now reassembled and it has been found that the pressure of the ball of the femoral prosthesis, if such a prosthesis is sued, or the natural ball shape of the bone acts to pressurize the cup and hold it in position while bone growth takes place.

It has been found that a cup of the kind described above has excellent wear qualities when made from the composite synthetic plastics material described.

The precise combination of thermoplastic polymeric material for the matrix and the pitch based carbon fiber can be established by experimentation but it has been found that preferably 20 to 40% by weight pitch based carbon fibers in a 60 to 80% by weight PEEK matrix and more preferably 30% by weight of carbon fibers in a 70% by weight PEEK matrix which has been machined in the manner described provides excellent wear qualities.

It has also been found that a prosthesis bearing component can be made using the materials and machining process which can be successfully employed in other types of prosthesis where there is conforming contact, for example, a shoulder prosthesis.

Further alternative applications to other types of prosthetic bearing components will be apparent to the man skilled in the art.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A prosthetic bearing component formed from a composite synthetic plastics material comprising an injection molded thermoplastic polymeric matrix reinforced by a pitch based carbon fiber and having a bearing surface which has been machined with a surface roughness with a value less than an $R_a$ of 2 μm wherein said bearing surface is or part spherical with a sphericity of 0.3 μm within a solid angle of 45°.

2. The prosthetic bearing component as claimed in claim 1 wherein said bearing surface shape is machined with tolerances of 0.1 to 0.15 mm.

3. The prosthetic bearing component as claimed in claim 1 wherein said composite material must be capable of withstanding a radiation value of at least 2.8 Mega Rads (Mrad).

4. The prosthetic bearing component as claimed in claim 1 which is in the form of a prosthetic hip cup.

5. The prosthetic bearing component as claimed in claim 1 wherein said thermoplastic polymeric matrix is made from a polyester, a polyonylketone, or a polysulphone.

6. The prosthetic bearing component as claimed in claim 5 wherein the polyester is PVT (polyethylene tetraphthalate), the polyonylketone is PEEK (polyether ether ketone) and the polysulphone is polyethersulphone.

7. The prosthetic bearing component as claimed in claim 1 which is the form of a cementless bearing element which has an outer surface which includes a number of raised engagement features.

8. The prosthetic bearing component as claimed in claim 7 wherein said engagement features are provided in directions extending from the outer periphery of the outer surface.

9. The prosthetic bearing component as claimed in claim 8 in which said engagement features are formed by projecting strakes of substantially triangular cross-section.

10. The prosthetic bearing component as claimed in claim 9 wherein the outer surface also carries one or more projecting fins.

11. A prosthetic bearing component formed from a composite synthetic plastics material com rising an injection molded thermoplastic polymeric matrix reinforced by a pitch based carbon fiber and having a bearing surface which has been machined with a surface roughness with a value less than $R^a$ of 2 μm wherein the combination of thermoplastic polymeric material for the matrix and the pitch bases carbon fibers is 20% to 40% by weight pitch based carbon fibers in a 60% to 80% by weight PEEK matrix.

12. The prosthetic bearing component as claimed in claim 11 in which the combination is 30% by weight carbon fibers in a 70% by weight PEEK matrix.

13. A carbon fiber reinforced bearing component comprising:

a part spherical body of a thermoplastic matrix having pitch based carbon fibers embedded therein, said carbon fibers being between 10 and 50 percent of the combined weight of the carbon fiber and thermoplastic, the bearing component body having an inner part spherical bearing surface with a roughness value less than an $R_a$ of 2 μm and has an outer surface including raised engagement features, the body has a pair of spaced apart arms with the inner bearing surface in the area of the arms being relieved with respect to said part spherical bearing surface wherein said bearing surface μm within a solid angle of 45°.

14. The carbon fiber reinforced bearing component as set forth in claim 13 wherein the carbon fiber is between 20 and 40 percent of the combined weight.

15. The prosthetic bearing component as claimed in claim 12 wherein said thermoplastic polymeric matrix is made from a polyester, a polyonylketone, or a polysulphone.

16. The prosthetic bearing component as claimed in claim 13 wherein the combination of polymeric material for the matrix and the pitch based carbon fibers is 20% to 40% by weight pitch based carbon fibers in a 60% to 80% by weight PEEK matrix.

17. The prosthetic bearing component as claimed in claim 16 in which the combination is 30% by weight carbon fibers in a 70% by weight PEEK matrix.

18. A carbon fiber reinforced bearing component comprising:
a part spherical body of a thermoplastic matrix having pitch based carbon fibers embedded therein, said carbon fibers being between 10 and 50 percent of the combined weight of the carbon fiber and thermoplastic, the bearing component body having an inner part spherical bearing surface with a roughness value less than an $R_a$ of 2 μm and has an outer surface including raised engagement features, the body has a pair of spaced apart arms with the inner bearing surface in the area of the arms being relieved with respect to said part spherical bearing surface and wherein the combination of polymeric material for the matrix and the pitch based carbon fibers is 20% to 40% b weight pitch based carbon fibers in a 60% to 80% by weight PEEK matrix.

* * * * *

UNITED STATES PATENT AND TRADEMARK OFFICE
CERTIFICATE OF CORRECTION

PATENT NO. : 6,638,311 B2  Page 1 of 1
DATED : October 28, 2003
INVENTOR(S) : Aiguo Wang et al.

It is certified that error appears in the above-identified patent and that said Letters Patent is hereby corrected as shown below:

Column 1,
Line 10, after "head" insert -- . --.
Line 10, "this" should read -- This --.
Line 12, "it" should read -- in --.
Line 14, "form" should read -- from --.
Line 19, after "replacements" insert -- " --.
Line 27, "id" should read -- is --.

Column 4,
Line 11, after "is" insert -- substantially --.
Line 44, "com rising" should read -- comprising --.
Line 48, "$R^a$" should read -- $R_a$ --.
Line 49, "bases" should read -- based --.

Column 5,
Line 7, "12" should read -- 13 --.

Column 6,
Line 14, "b" should read -- by --.

Signed and Sealed this

Ninth Day of March, 2004

JON W. DUDAS
*Acting Director of the United States Patent and Trademark Office*